United States Patent [19]

Mason

[11] Patent Number: 5,417,720
[45] Date of Patent: May 23, 1995

[54] NONAMBIENT TEMPERATURE PAD CONFORMABLE TO A BODY FOR THERAPEUTIC TREATMENT THEREOF

[75] Inventor: Bradley R. Mason, Olivenhain, Calif.

[73] Assignee: Breg, Inc., Vista, Calif.

[21] Appl. No.: 300,699

[22] Filed: Sep. 2, 1994

Related U.S. Application Data

[63] Continuation of Ser. No. 69,195, May 27, 1993, abandoned, which is a continuation-in-part of Ser. No. 906,407, Jul. 1, 1992, Pat. No. 5,324,319, and Ser. No. 851,345, Mar. 12, 1992, Pat. No. Des. 345,609, said Ser. No. 906,407, and Ser. No. 851,345, each is a continuation-in-part of Ser. No. 767,494, Sep. 30, 1991, Pat. No. 5,241,951, which is a continuation-in-part of Ser. No. 578,508, Sep. 5, 1990, Pat. No. 5,080,089.

[51] Int. Cl.⁶ .................................................. A61F 7/00
[52] U.S. Cl. ......................................... 607/104; 607/108
[58] Field of Search ................... 607/96, 104, 108–112, 607/114

[56] References Cited

U.S. PATENT DOCUMENTS

| | | | |
|---|---|---|---|
| 4,061,898 | 12/1977 | Murray et al. | 607/110 X |
| 4,108,146 | 8/1978 | Golden | 607/104 |
| 4,357,009 | 11/1982 | Baker | 607/111 X |
| 4,753,242 | 6/1988 | Saggers | 607/110 X |
| 4,947,843 | 8/1990 | Wright et al. | 607/96 |
| 5,014,695 | 5/1991 | Benak et al. | |
| 5,086,771 | 2/1992 | Molloy. | |

*Primary Examiner*—Angela D. Sykes
*Attorney, Agent, or Firm*—Rodney F. Brown

[57] ABSTRACT

A pad is provided for therapeutically treating bodily injuries or ailments by positioning the pad on an affected part of the body and circulating a nonambient temperature treatment fluid through the pad. The pad has a bladder that is a symmetrical planar member configured in sections conformable to the contours of the body, thereby facilitating heat exchange between the pad and the patient. Included are a relatively wide main section and extension section that are fluid-communicatively joined with one another at the axis of symmetry across a relatively narrow connective section. The extension section is oblong-shaped, having a longitudinal axis aligned substantially perpendicular to the axis of symmetry and substantially parallel to the forward and rearward edges of the planar member.

19 Claims, 3 Drawing Sheets

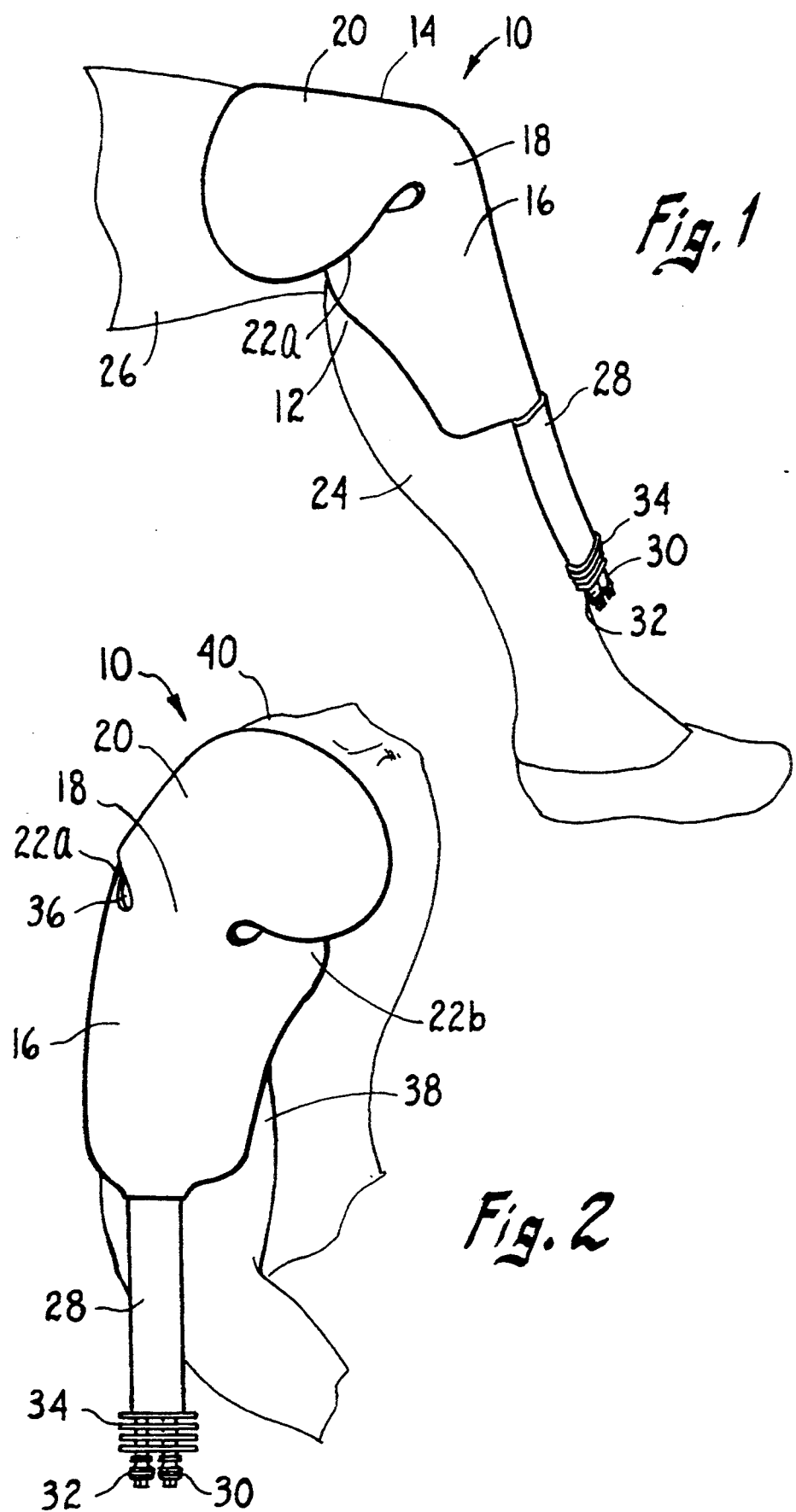

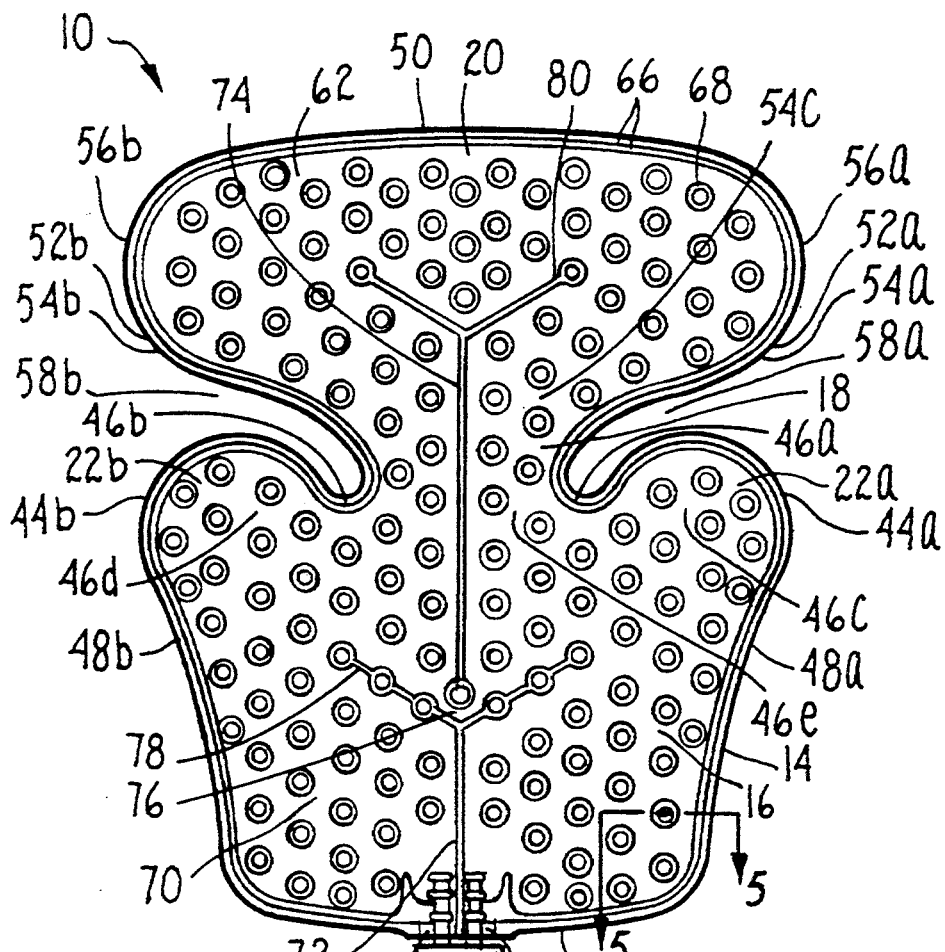
Fig. 3
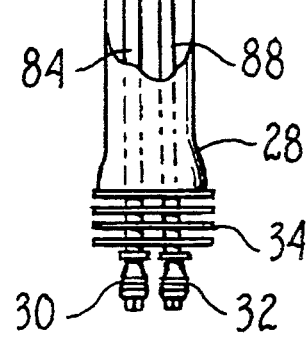
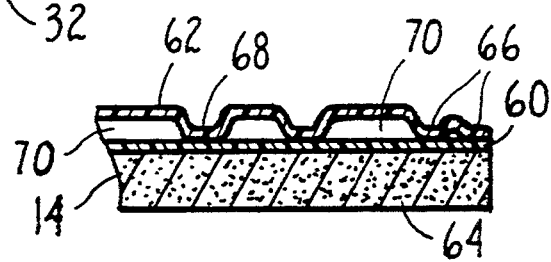
Fig. 5

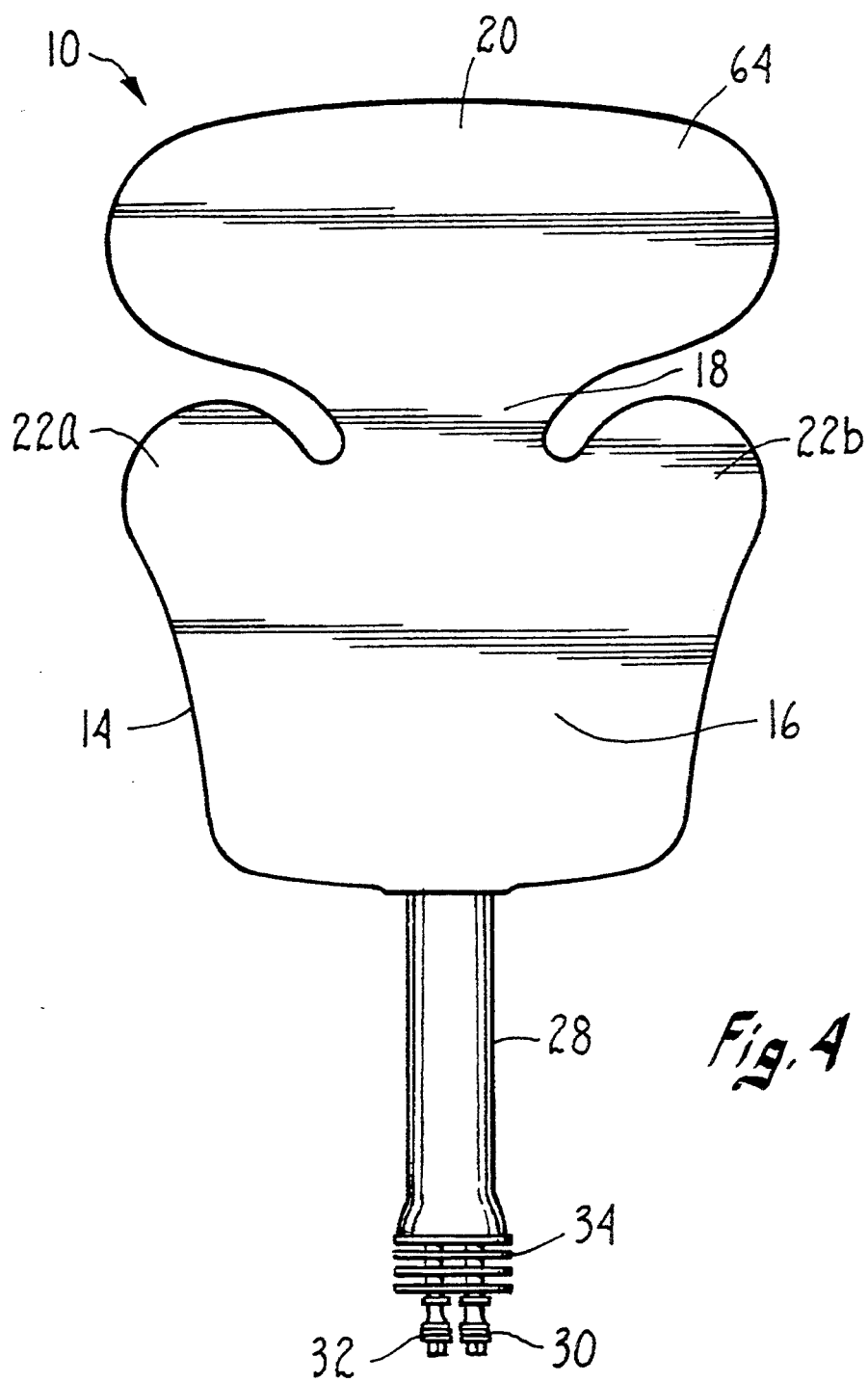

NONAMBIENT TEMPERATURE PAD CONFORMABLE TO A BODY FOR THERAPEUTIC TREATMENT THEREOF

This application is a continuation patent application of our prior patent application Ser. No. 08/069,195, filed May 27, 1993, now abandoned, which is a continuation-in-part patent application of our prior utility patent application entitled, "Gravity Driven Therapeutic Fluid Circulation Device", Ser. No. 07/906,407, filed on Jul. 1, 1992, now U.S. Pat. No. 5,324,319, and is also a continuation-in-part patent application of our prior design patent application entitled "Therapeutic Fluid Circulation Pad", Ser. No. 07/851,345, filed on Mar. 12, 1992, now U.S. Pat. No. D345,609.

Both patent applications, Ser. Nos. 07/906,407 (U.S. Pat. No. 5,324,319) and 07/851,345 (U.S. Pat. No. D345,609), are continuation-in-part patent applications of our prior patent application entitled, "Therapeutic Nonambient Temperature Fluid Circulation System", Ser. No. 07/767,494, filed on Sep. 30, 1991, now U.S. Pat. No. 5,241,951 which is a continuation-in-part patent application of our patent application entitled, "Therapeutic Apparatus Applying Compression and a Nonambient Temperature Fluid," Ser. No. 07/578,508, filed on Sep. 5, 1990 and now issued as U.S. Pat. No. 5,080,089.

TECHNICAL FIELD

The present invention relates generally to therapeutic treatment of the body, and more particularly to a pad that is positioned on and conforms to an affected part of the body to therapeutically cool or heat the affected body part with a nonambient temperature fluid circulated through the pad.

BACKGROUND OF THE INVENTION

Bodily injuries and ailments are commonly treated by applying a nonambient temperature material to the affected area of the body. For example, low temperature material, typically in the form of ice or a cold liquid, advantageously inhibits swelling in the region of the injury. A high temperature material, typically applied in the form of hot water or an active heating element, advantageously reduces pain and promotes healing.

A number of devices have been developed for continuously treating an injury at a controlled low temperature by circulating a cooling fluid between a low temperature fluid reservoir and a cooling pad positioned on the desired body location of a patient. Such devices are typified by U.S. Pat. Nos. 4,149,529 to Copeland et al; and 4,962,761 to Golden. As is apparent, the treatment efficiency of the cooling pad is optimal when the heat exchange surface of the pad has maximum contact with the body location being treated to facilitate heat exchange between the body and pad. Accordingly, both of the above-referenced patents disclose cooling pads that desirably conform to the contours of the body.

Nevertheless, the performance of such prior art pads has been found to be unsatisfactory. The pad of Copeland et al uniquely fits only one particular body part and body size. Thus, a whole range of pads must be maintained in inventory to accommodate treatment of different body parts and body sizes. Although the cooling pad of Golden has a more generic configuration, it is not readily conformable to rounded body parts, such as knee joints, without employing an intervening cushion which diminishes the heat exchange performance of the pad.

U.S. Pat. No. 5,086,771 to Molloy discloses a cooling pad that attempts to overcome these problems. Although the pad of Molloy has been found to have somewhat improved conformance characteristics, its restrictive flow channel nevertheless has a tendency to kink when closely configured to certain body contours. It has also been found that the restrictive flow channel of the Molloy pad does not produce a sufficiently uniform temperature distribution across the pad.

Accordingly, it is an object of the present invention to provide a nonambient temperature treatment pad that is closely conformable to virtually any body contour. It is another object of the present invention to provide a treatment pad having a fluid flowpath therethrough which is not substantially kinked or otherwise impeded when the pad is conformed to a body contour. It is yet another object of the present invention to provide a treatment pad that maintains a substantially uniform temperature distribution across its heat exchange surface when the pad is conformed to a body contour.

SUMMARY OF THE INVENTION

The present invention is a device for therapeutically treating bodily injuries or ailments with a nonambient temperature treatment fluid. The device is a pad positionable on an affected part of the body of a patient to either cool or heat the body part, depending on the temperature of the treatment fluid contained within the pad. The treatment fluid is circulated through the pad while the pad is in place on the desired body part, thereby enabling heat exchange between the body part and the treatment fluid.

The configuration of the pad renders it readily and fully conformable to the contours of the body part on which it is positioned. Conformance of the pad to the body of the patient enables a large fraction of the pad surface area to contact the body, advantageously facilitating heat exchange between the pad and the patient.

The pad has a substantially planar member made up of an upper sheet of a thin flexible heat-conductive material overlaying a substantially identical lower sheet of the same material. The sheets are sealingly bonded together around their periphery to form a bladder enclosing an internal flow channel for the treatment fluid. The planar member is substantially symmetrical and is characterizable as having a plurality of interconnected fluid-communicating sections that are uniquely and correspondingly configured about the axis of symmetry of the planar member to provide close conformance of the pad to the body contours of the patient.

In particular, the planar member has a relatively wide main section and a relatively wide extension section that are fluid-communicatively joined with one another across a relatively narrow connective section. The extension section is oblong-shaped, having a longitudinal axis aligned substantially perpendicular to the axis of symmetry of the planar member and substantially parallel to the forward and rearward edges of the planar member. Dimensionally, the width of the extension section, defined by the length of its longitudinal axis, is substantially greater than the width of the connective section. Likewise, the width of the main section, defined by the length of its forward border, is substantially greater than the width of the connective section.

Engagement of the relatively narrow connective section with the relatively wide main and extension sections is centrally provided about the axis of symmetry, thereby resulting in lateral void spaces on opposite sides of the connective section. A pair of arcuate-shaped nubs forwardly extend from the main section into each void space, although the extension distance of each nub is less than the height of the connective section, preventing the nubs from entirely filling the void spaces.

The internal flow channel between the upper and lower sheets is delineated by a first linear flow divider positioned along the axis of symmetry of the planar member entirely within the main section. Consequently, the first flow divider is aligned substantially perpendicular to the forward border of the main section and the longitudinal axis of the extension section. A second linear flow divider is also provided in linear alignment with the first flow divider, but spaced a small distance therefrom to define a narrow breach between the two flow dividers within the main section.

The linear flow dividers are so aligned to maintain the internal flow channel divided along portions of the axis of symmetry and provide a tortuous pathway for the treatment fluid through the flow channel. A plurality of isolated circular flow diverters are also periodically distributed throughout the internal flow channel to increase the tortuosity of the pathway. The tortuous pathway through the flow channel effectively creates a desirable uniform temperature distribution across the face of the planar member.

Selective fluid communication between the internal flow channel and an outside fluid source is provided by an inlet tube entering the pad via an inlet port in the main section and by an outlet tube exiting the pad via an outlet port in the main section. The ports are proximally positioned on opposite sides of the first linear flow divider to prevent substantial mixing between the treatment fluid at its initial entry and exit points. Shutoff valves are fitted across the exterior end of each tube, which are biased in the closed position. Thus, fluid communication between the interior and exterior of the pad requires active opening of the valves.

In use, the pad is conformable to virtually any body part, particularly to contoured body parts, and more particularly to body right-angled joints, such as the shoulder, knee, elbow and hip joints. The specific sectionalized configuration of the pad reduces the likelihood of kinking in peripheral regions of the pad, including the extension section and nubs, when conformed to contoured body parts. Should kinking occur in these peripheral regions however, the narrow breach between the flow dividers enables sufficient fluid flow through the pad to continue effective treatment of the affected body part.

The present invention will be further understood, both as to its structure and operation, from the accompanying drawings, taken in conjunction with the accompanying description, in which similar reference characters refer to similar parts.

BRIEF DESCRIPTION OF THE DRAWINGS

FIG. 1 is a perspective view of the conformable pad of the present invention positioned on the knee of a patient.

FIG. 2 is a perspective view of the conformable pad of the present invention positioned on the shoulder of a patient.

FIG. 3 is a bottom plan view of the conformable pad of the present invention.

FIG. 4 is a top plan view of the conformable pad of the present invention.

FIG. 5 is a cross-sectional elevational view of the conformable pad of the present invention taken along line 5—5 of FIG. 3.

DESCRIPTION OF PREFERRED EMBODIMENTS

Referring initially to FIG. 1, the pad of the present invention, generally designated 10, is shown operatively positioned on the knee joint 12 of a patient being therapeutically treated. The pad 10 comprises a planar member 14 having a main section 16, a connective section 18, an extension section 20. A pair of lateral nubs 22a, 22b extend from the main section 16 (although only nub 22a is visible in FIG. 1).

The connective section 18 rests directly atop the patella of knee joint 12 and conforms thereto. Main section 16 fluid-communicatively engages connective section 18 and wraps around the lower leg 24 proximal knee joint 12 in conformance with the curvature thereof. The extension section 20 likewise fluid-communicatively engages connective section 18 and conformingly wraps around the upper leg 26 proximal knee joint 12. Nub 22a fits under extension section 20 to contact the lateral portion of knee joint 12.

Pad 10 further comprises an insulative sheath 28 extending rearwardly from the main section 16 of planar member 14. Sheath 28 encases a pair of inlet and outlet tubes (not shown in FIG. 1, but described hereafter with reference to subsequent Figures). A male inlet valve coupling 30 and a male outlet valve coupling 32 are shown in FIG. 1 extending rearwardly from sheath 28. A grip 34 is provided to facilitate manual engagement and release of male valve couplings 32, 34 with corresponding female valve couplings of a fluid supply system (not shown).

Referring to FIG. 2, pad 10 is shown operatively positioned on the shoulder joint 36 of a patient being therapeutically treated. The connective section 18 rests directly on the tip of the shoulder joint 36 and conforms thereto. Main section 16 wraps around the upper arm 38 proximal shoulder joint 36 in conformance with the curvature thereof. The extension section 20 likewise conformingly wraps around the top 40 of shoulder joint 36. Nubs 22a and 22b fit under extension section 20 to contact the lateral portions of shoulder joint 36.

The positioning of pad 10 on the knee joint 12 and shoulder joint 36 is shown in FIGS. 1 and 2 by way of example. It is apparent to one skilled in the art that pad 10 can be operatively positioned on other similarly contoured body parts, including the elbow and hip joints, in the same manner as set forth above. It is further noted that a conventional elastic wrap can be used to secure the position of pad 10 on the desired body part in a manner well known to one skilled in the art.

The configuration and construction of pad 10 are described hereafter with reference to FIGS. 3–5. For purposes of specifying the relative shapes and dimensions of the pad sections, pad 10 is described hereafter as laid out flat on a planar surface in a symmetrical configuration. Nevertheless, as noted above, the components of pad 10 are generally flexible and, thus, capable of assuming a number of different contoured configurations when the pad 10 is operational.

Referring initially to FIG. 3, the main section 16 of planar member 14 has a quadrilateral-like shape with approximately linear forward and rearward borders that are substantially parallel to one another and perpendicular to the axis of symmetry of planar member 14. The rearward border of main section 16 corresponds to the exposed rearward edge 42 of planar member 14, whereas the forward border of main section 16 extends between endpoints 44a and 44b, with only portions 46a and 46b of the forward border being exposed. The remaining portions 46c, 46d, and 46e of the forward border fluid-communicatively engage arcuate-shaped lobular nubs 22a, 22b and connective section 18, respectively.

Main section 16 further has opposing lateral borders that correspond to the exposed lateral edges 48a and 48b of main section 16, respectively. Lateral edges 48a, 48b taper toward one another in the rearward direction. Accordingly, the length of the forward border, as defined by the distance between endpoints 44a, 44b, is greater than the length of the rearward border, as defined by the length of rearward edge 42.

The extension section 20 of planar member 14 has an oblong shape with rounded lateral borders and approximately linear forward and rearward borders that are substantially parallel to one another. The forward border of extension section 20 corresponds to the exposed forward edge 50 of planar member 14, whereas the rearward border of extension section 20 extends between endpoints 52a and 52b, with only portions 54a and 54b being exposed. The remaining portion 54c of the rearward border engages connective section 18.

Extension section 20 has a longitudinal axis extending between endpoints 56a, 56b. The longitudinal axis of extension section 20 is aligned substantially perpendicular to and bisected by the axis of symmetry of planar member 14. the longitudinal axis is further aligned substantially parallel to the forward and rearward borders of main section 16, as well as substantially parallel to the forward and rearward borders of extension section 20. The longitudinal axis has a length, as defined by the distance between endpoints 56a, 56b, greater than or substantially equal to the length of the forward border of main section 16.

One end of connective section 18 centrally engages main section 16 at the axis of symmetry of planar member 14 and continuously engages main section 16 in both lateral directions therefrom, across the entire portion 46e of its forward border which extends between portions 46a and 46b. Similarly, the opposite end of connective section 18 centrally engages extension section 20 at the axis of symmetry of planar member 14 and continuously engages extension section 20 in both lateral directions therefrom, across the entire portion 54c of its rearward border which extends between portions 54a and 54b.

The width of extension section 20, as defined by the length of its longitudinal axis, and the width of the main section 16, as defined by the length of its forward border, are each greater than the width of the connective section 18, as determined at any point along its height. Accordingly, the widths of extension section 20 and main section 16 are each greater than the narrowmost width of connective section 18, shown herein to be the length of portion 46e, and are each likewise greater than the broadmost width of connective section 18, shown herein to be the length of portion 54c.

The relative positioning of sections 16, 18, 20 provides lateral void spaces 58a, 58b on opposite sides of connective section 18 between the forward border of main section 16 and the rearward border of extension section 20, respectively. The nubs 22a, 22b are arcuate-shaped, resembling lobes forwardly extending from portions 46c, 46d into void spaces 58a, 58b, respectively. The forward extension distance of each nub 22a, 22b, however, is less than the height of connective section 20, as defined by the distance between portions 46e and 54c. Accordingly, nubs 22a, 22b do not close off lateral void spaces 58a, 58b, respectively when planar member 14 is in a flattened condition.

With reference to FIGS. 4 and 5, and continuing reference to FIG. 3, planar member 14 is shown to have a laminar construction, including an upper sheet 60 and a lower sheet 62 both formed from a thin flexible heat-conductive material, such as polyurethane. Lower sheet 62 is shown in FIGS. 3 and 5 to be transparent and exposed so that it directly contacts the body when pad 10 is operatively positioned thereon. In contrast, upper sheet 60 is sandwiched between lower sheet 62 and a relatively thicker insulative layer 64 of a flexible foam that is bonded to upper sheet, as shown in FIGS. 4 and 5. Insulative layer 64 prevents heat loss to the surrounding atmosphere, or alternatively heat gain therefrom, depending on the temperature of the treatment fluid.

The peripheries of sheets 60, 62 are bonded to one another by duplicate thermal welding to substantially enclose the interior of sheets 60, 62 within a secure peripheral seam 66, thereby defining a bladder. A plurality of circular welds 68 also bond sheets 60, 62 together at periodic points across the planar member surface. Consequently, a continuous fluid-communicative space remains between sheets 60, 62 where the sheets are not bonded to one another. This space constitutes an internal flow channel 70 for treatment fluid being circulated through pad 10. The circular welds 68 function to limit the height of flow channel 70 when operating under elevated pressure, and also function to divert fluid flow in a tortuous path through flow channel 70.

Further construction details with respect to specific materials having utility in the present invention, as well as to specific methods for bonding the materials together as required by the present invention, are well known in the art, for example, as disclosed in U.S. Pat. No. 5,086,771. Accordingly, U.S. Pat. No. 5,086,771 is incorporated herein by reference.

As shown in FIG. 3, flow channel 70 is delineated by a first linear flow divider 72 that is formed from a discrete linear weld, bonding sheets 60, 62 together along the length of the weld. The first flow divider 72 is contained entirely within main section 16, and is aligned along the axis of symmetry of planar member 14, substantially perpendicular to the forward and rearward borders of main section 16 as well as the longitudinal axis of extension section 20. The flow divider 72 engages seam 66 at the rearward edge 42 of the planar member to substantially prevent continuous fluid flow along edge 42.

Flow channel 70 is further delineated by a second discrete linear flow divider 74 formed in the same manner as flow divider 72. Second flow divider 74 is in linear alignment with first flow divider 72 along the axis of symmetry of planar member 14, but is spaced a small distance apart from the first flow divider 72 to define a narrow breach 76 between flow dividers 72, 74. Second flow divider 74 extends from extension section 20 through connective section 18 to main section 16, such that breach 76 is positioned within main section 16.

It is noted that narrow breach 76 enables a limited degree of cross flow within the flow channel 70 of main section 16, thereby improving temperature distribution across planar member 14 during operation of the pad, and enabling continued operation of the pad 10 should kinks occur in sections 18, 20 or nubs 22a, 22b. Flow distribution within flow channel 70 is also enhanced by providing orthogonally or diagonally oriented branches 78, 80 on the respective forward ends of first and second flow dividers 72, 74.

An inlet port 82 provides an opening in seam 66 at rearward edge 42 of planar member 14 slightly offset to one side of the first linear flow divider 72. A flexible inlet tube 84 penetrates the internal flow channel 70 through inlet port 82 and is sealingly bonded to sheets 60, 62 proximal inlet port 82. Inlet tube 84 extends rearwardly from inlet port 82 to selectively provide fluid communication between the internal flow channel 70 and the exterior of the pad 10.

A male shutoff valve coupling 30 of the type disclosed in our copending U.S. patent application Ser. No. 07/906,409, incorporated herein by reference, is fitted across the exterior end of inlet tube 84. Valve coupling 30 is biased in the closed position, but can be actively maintained open to provide fluid communication between the interior and exterior of the pad 10 by means of a corresponding female valve coupling (not shown) of the type disclosed in our above-referenced patent application.

An outlet port 86 is similarly provided in seam 66 substantially adjacent to inlet port 82, but slightly offset to the opposite side of the first linear flow divider 72. An outlet tube 88 extends from outlet port 86 and likewise has a male shutoff valve coupling 32 across its exterior end. Both inlet and outlet tubes 84, 88 are enclosed, as shown by cut-away in FIG. 3, within the insulative sheath 28 preferably formed from a flexible foam.

In operation, inlet tube 84 and outlet tubes 88 are connected to a system (not shown) for driving a nonambient temperature therapeutic treatment fluid from a fluid reservoir, through the internal flow channel 70 of pad 10, and back to the reservoir. Such systems having utility with pad 10 are disclosed in our copending U.S. patent applications, Ser. Nos. 07/906,407 and 07/767,494, both of which are incorporated herein by reference.

While the forgoing preferred embodiments of the invention have been described and shown, it is understood that alternatives and modifications, such as those suggested and others, may be made thereto and fall within the scope of the invention.

We claim:

1. A pad positionable on a body part of a patient to therapeutically treat the body part with a nonambient temperature fluid flowing through said pad, said pad comprising:

a substantially planar bladder that is flexible to enable conformance of said substantially planar bladder to a desired three-dimensional body part, said bladder configured in a plurality of fluid-communicating sections including a main section having a forward border and a rearward border, an extension section positioned forward of said main section having a longitudinal axis of a fixed length aligned substantially parallel to said forward border, and a connective section centrally engaging said extension section and said main section, wherein said connective section has a width substantially less than said fixed length of said longitudinal axis;

a hollow fluid port providing fluid communication between the interior and exterior of said bladder; and a hollow internal fluid flow channel positioned in the interior of said bladder in fluid communication with said fluid port and providing fluid communication between said plurality of sections.

2. A pad as recited in claim 1 wherein said main section has a width substantially greater than said width of said connective section.

3. A pad as recited in claim 1 wherein said bladder is formed from an upper sheet and a lower sheet.

4. A pad as recited in claim 1 wherein said extension section is oblong-shaped.

5. A pad as recited in claim 1 wherein said main section has a first nub forwardly extending a first extension distance from said forward border on one side of said connective section, and a second nub forwardly extending a second extension distance from said forward border on an opposite side of said connective section, further wherein said connective section has a length greater than said first or second extension distances.

6. A pad as recited in claim 5 wherein said first and second nubs are arcuate-shaped.

7. A pad as recited in claim 1 further comprising a first linear flow divider delineating said internal flow channel and contained entirely within said main section, wherein said first linear flow divider is aligned substantially perpendicular to said longitudinal axis of said extension section.

8. A pad as recited in claim 7 further comprising a second linear flow divider in linear alignment with said first linear flow divider and spaced a distance therefrom to define a breach therebetween, wherein said second linear flow divider delineates said internal flow channel within said connective section and said breach is positioned within said main section.

9. A pad as recited in claim 8 wherein said bladder is symmetrical, having an axis of symmetry, and further wherein said first and second linear flow dividers are aligned on said axis of symmetry.

10. A pad as recited in claim 9 wherein said longitudinal axis is aligned substantially perpendicular to said axis of symmetry and said axis of symmetry substantially bisects said longitudinal axis.

11. A pad as recited in claim 7 wherein said fluid port is a fluid inlet port entering said rearward border of said main section and said pad further comprises a fluid outlet port exiting said rearward border of said main section, said fluid inlet and outlet ports in fluid communication with said internal flow channel and separated from one another by said first linear flow divider.

12. A pad positionable on a body part of a patient to therapeutically treat the body part with a nonambient temperature fluid flowing through said pad, said pad comprising:

a substantially planar bladder that is flexible to enable conformance of said substantially planar bladder to a desired three-dimensional body part, said bladder having an axis of symmetry and configured in a plurality of fluid-communicating sections including a main section, an extension section having a longitudinal axis of a fixed length aligned substantially perpendicular to said axis of symmetry, and a connective section connecting said extension section and said main section on said axis of symmetry, wherein said connective section has a width substantially less than said fixed length of said longitudinal axis;

a hollow fluid port providing fluid communication between the interior and exterior of said bladder; and a hollow internal fluid flow channel positioned in the interior of said bladder in fluid communication with said fluid port and providing fluid communication between said plurality of sections.

13. A pad as recited in claim 12 wherein said extension section is oblong-shaped.

14. A pad as recited in claim 12 wherein said axis of symmetry substantially bisects said longitudinal axis.

15. A pad as recited in claim 12 further comprising a first linear flow divider delineating said internal flow channel and contained entirely within said main section, wherein said first linear flow divider is aligned substantially perpendicular to said longitudinal axis of said extension section.

16. A pad as recited in claim 15 further comprising a second linear flow divider in linear alignment with said first linear flow divider and spaced a distance therefrom to define a breach therebetween, wherein said second linear flow divider delineates said internal flow channel within said connective section and said breach is positioned within said main section.

17. A pad as recited in claim 12 wherein said main section has a width substantially greater than said width of said connective section.

18. A pad as recited in claim 12 wherein said main section has a width less than or equal to said fixed length of said longitudinal axis.

19. A pad as recited in claim 12 wherein said main section has a first nub forwardly extending a first extension distance from said main section on one side of said connective section, and a second nub forwardly extending a second extension distance from said main section on an opposite side of said connective section, further wherein said connective section has a length greater than said first or second extension distances.

* * * * *

UNITED STATES PATENT AND TRADEMARK OFFICE
CERTIFICATE OF CORRECTION

PATENT NO. : 5,417,720
DATED : May 23, 1995
INVENTOR(S) : Bradley R. Mason, et al It is certified that error appears in the above-indentified patent and that said Letters Patent is hereby corrected as shown below:

On the title page, under item [19], after Mason, add --et al.--
On the title page, item [75], add --Jeffrey T. Mason, Escondido, Calif.--.

Signed and Sealed this

Twenty-ninth Day of August, 1995

*Attest:*

BRUCE LEHMAN

*Attesting Officer*    *Commissioner of Patents and Trademarks*